United States Patent
Kohlstruk et al.

(10) Patent No.: US 7,339,074 B2
(45) Date of Patent: *Mar. 4, 2008

(54) MULTISTAGE CONTINUOUS PREPARATION OF CYCLOALIPHATIC DIISOCYANATES

(75) Inventors: Stephan Kohlstruk, Dülmen (DE); Manfred Kreczinski, Herne (DE); Rainer Elm, Marl (DE); Hans-Werner Michalczak, Herne (DE)

(73) Assignee: Degussa AG, Düsseldorf (DE)

( * ) Notice: Subject to any disclaimer, the term of this patent is extended or adjusted under 35 U.S.C. 154(b) by 523 days.

This patent is subject to a terminal disclaimer.

(21) Appl. No.: 10/922,910

(22) Filed: Aug. 23, 2004

(65) Prior Publication Data

US 2005/0043563 A1 Feb. 24, 2005

(30) Foreign Application Priority Data

Aug. 22, 2003 (DE) ................ 103 38 509

(51) Int. Cl.
*C07C 263/00* (2006.01)
(52) U.S. Cl. ..................................... 560/345
(58) Field of Classification Search ............ None
See application file for complete search history.

(56) References Cited

U.S. PATENT DOCUMENTS

| | | | |
|---|---|---|---|
| 2,692,275 A | 10/1954 | Bortnick et al. | |
| 3,919,279 A | 11/1975 | Rosenthal et al. | |
| 4,081,472 A | 3/1978 | Tsumura et al. | |
| 4,268,683 A | 5/1981 | Gurgiolo | |
| 4,386,033 A | 5/1983 | Koenig et al. | |
| 4,388,246 A | 6/1983 | Sundermann et al. | |
| 4,530,796 A | 7/1985 | Mattner et al. | |
| 4,596,678 A | 6/1986 | Merger et al. | |
| 4,596,679 A | 6/1986 | Hellbach et al. | |
| 4,692,550 A | 9/1987 | Engbert et al. | |
| 4,713,476 A | 12/1987 | Merger et al. | |
| 4,851,565 A | 7/1989 | Merger et al. | |
| 5,087,739 A | 2/1992 | Bohmholdt et al. | |
| 5,360,931 A | 11/1994 | Bohmholdt et al. | |
| 5,386,053 A * | 1/1995 | Otterbach et al. | 560/344 |
| 5,453,536 A | 9/1995 | Dai et al. | |
| 5,502,244 A | 3/1996 | Okawa et al. | |
| 5,616,784 A | 4/1997 | Schwarz et al. | |
| 5,646,328 A | 7/1997 | Deibele et al. | |
| 5,744,633 A | 4/1998 | Wilmes et al. | |
| 5,962,728 A | 10/1999 | Mason et al. | |
| 6,204,409 B1 | 3/2001 | Aso et al. | |
| 2005/0043563 A1 | 2/2005 | Kohlstruk et al. | |

FOREIGN PATENT DOCUMENTS

| | | |
|---|---|---|
| DE | 1 022 222 | 1/1958 |
| DE | 26 35 490 | 2/1977 |
| DE | 196 27 552 A1 | 1/1998 |
| DE | 101 27 273 | 12/2002 |
| EP | 0 018 586 | 11/1980 |
| EP | 0 054 817 | 6/1982 |
| EP | 0 061 013 | 9/1982 |
| EP | 0 355 443 | 2/1990 |
| EP | 0 566 925 | 10/1993 |
| EP | 0 568 782 | 11/1993 |
| EP | 0 568 782 A2 | 11/1993 |
| EP | 0 657 420 | 6/1995 |
| EP | 0 990 644 | 4/2000 |

OTHER PUBLICATIONS

U.S. Appl. No. 11/100,603, filed Apr. 7, 2005, Kohlstruk, et al.
U.S. Appl. No. 11/101,428, filed Apr. 8, 2005, Kohlstruk, et al.
U.S. Appl. No. 11/185,776, filed Jul. 21, 2005, Kohlstruk, et al.
U.S. Appl. No. 10/917,463, filed Aug. 13, 2004, Kohlstruk, et al.
U.S. Appl. No. 10/922,910, filed Aug. 23, 2004, Kohlstruk, et al.
U.S. Appl. No. 10/921,934, filed Aug. 20, 2004, Kohlstruk, et al.

* cited by examiner

*Primary Examiner*—Yvonne Eyler
*Assistant Examiner*—Kellette Gale

(57) ABSTRACT

The invention relates to a multistage process for continuous and phosgene-free preparation of cycloaliphatic diisocyanates.

43 Claims, No Drawings

MULTISTAGE CONTINUOUS PREPARATION OF CYCLOALIPHATIC DIISOCYANATES

BACKGROUND OF THE INVENTION

1. Field of the Invention

The invention relates to a multistage process for continuous and phosgene-free preparation of cycloaliphatic diisocyanates.

2. Discussion of the Background

The synthetic access route to isocyanates may be via a series of different routes. The variant for industrial scale preparation of isocyanates which is the oldest and still predominates today is what is known as the phosgene route. This process is based on the reaction of amines with phosgene. A disadvantage of the phosgene process is the use of phosgene which, as a consequence of its toxicity and corrosivity, places particularly high requirements on its handling on the industrial scale.

There are several processes which avoid the use of phosgene for preparing isocyanates on the industrial scale. The term phosgene-free process is frequently used in connection with the conversion of amines to isocyanates using alternative carbonylating agents, for example urea or dialkyl carbonate (EP 0018586, EP 0355443, U.S. Pat. No. 4,268, 683, EP 0990644).

The urea route is based on the urea-mediated conversion of diamines to diisocyanates via a two-stage process. In the first step, a diamine is reacted with alcohol in the presence of urea or urea equivalents (for example alkyl carbonates, alkyl carbamates) to give a diurethane which typically passes through an intermediate purification stage and is then thermally cleaved in the second step to diisocyanate and alcohol (EP 0355443, U.S. Pat. No. 4,713,476, U.S. Pat. No. 5,386,053). Alternatively, the actual urethane formation may also be preceded by the separate preparation of a diurea by selectively reacting the diamine with urea (EP 0568782). Also conceivable is a two-stage sequence consisting of partial reaction of urea with alcohol in the first and subsequent metering in and urethanization of the diamine in the second step (EP 0657420).

The thermal cleavage of urethanes to the corresponding isocyanates and alcohols has been known for some time and can be carried out either in the gas phase at high temperatures or at relatively low temperatures in the liquid phase. However, a problem in both procedures is that the thermal stress inevitably also causes undesired side reactions to take place which firstly reduce the yield and secondly lead to the formation of resinifying by-products which considerably disrupt the course of an industrial process as a result of deposits and blockages in reactors and workup apparatus.

There has therefore been no shortage of suggestions of chemical and process technology measures to achieve yield improvements and limit the undesired by-product formation. For instance, a series of documents describes the use of catalysts which accelerate the cleavage reaction of the urethanes (DE 1022222, U.S. Pat. No. 3,919,279, DE 2635490). Indeed, it is entirely possible in the presence of suitable catalysts, which are a multitude of basic, acidic and also organometallic compounds, to increase the isocyanate yield in comparison to the uncatalyzed variant. However, the formation of undesired by-products can also not be prevented by the presence of a catalyst. The same applies to the additional use of inert solvents, as recommended in U.S. Pat. No. 3,919,279 and DE 2635490, in order to ensure uniform distribution of the heat supplied and of the catalyst in the reaction medium. However, the use of solvents boiling under reflux fundamentally has the consequence of a reduction in the space-time yield of isocyanates and is additionally hindered with the disadvantage of additional high energy demands.

Examples which are cited in EP 0054817 for thermal catalyzed cleavage of monourethanes describe the partial discharge of the reaction mixture to remove resinifying by-products formed in the course of the urethane cleavage. This procedure serves to prevent deposits and blockages in reactors and workup units. There are no indications which point to a yield-increasing utilization of the partial discharge. EP 0061013 describes a similar approach to a solution, in which the thermolysis is in this case carried out in the presence of solvents whose purpose is apparently to better absorb the involatile by-products. Here also, the partial discharge is not utilized for the purposes of yield optimization.

EP 0355443 discloses that a yield increase can be achieved when the higher molecular weight by-products which can and cannot be utilized and are formed in the cleavage reactor during the cleavage of diurethanes, to ensure a disruption-free and selective reaction, are discharged substantially continuously out of the reactor and subsequently converted for the most part in the presence of alcohol and then recycled into the diurethane preparation. The procedure described is associated with high energy demands, since nonutilizable by-products are removed from the effluent of the diurethane preparation by distillation, and all of the diurethane has to be evaporated. In contrast to EP 0355443, the urethanization effluent in the process of EP 0566925 is divided into two substreams of which only one is freed by distillation of its high-boiling, nonutilizable by-products, before the combined diurethane streams are fed to the deblocking reaction in the cleavage reactor. In addition, the continuous cleavage reactor discharge in EP 0566925 is recycled directly, i.e. without a reurethanization step, into the diurethane synthesis.

The preparation of the diurethanes in a one-pot reaction from urea, diamine and alcohol with simultaneous removal of ammonia is common practice and is described in a series of patents (EP 0018568, EP 0355443, EP 0566925). A disadvantage is that the simultaneous reaction of urea, alcohol and diamine results in the inevitable formation of large amounts of by-products which impair the selectivity of the reaction and have to be removed before the thermal deblocking of diurethanes. EP 0568782 therefore claims a continuous process for preparing (cyclo)aliphatic diisocyanates, which comprises essentially three main steps, of which the first describes the formation of bisureas, the second the formation of diurethanes from the bisureas and the third the cleavage of the diurethanes in the liquid phase to the desired diisocyanates, i.e. the diurethane is prepared in two separate stages. According to the teaching of EP 0568782, the throughput of the reaction sequence of bisurea formation and subsequent diurethane synthesis is initially freed by distillation of low and middle boilers such as alcohols, carbamates and carbonates and the high boilers in the diurethane are then removed by short-path evaporation. The diurethane is thermally deblocked and a portion of the cleavage residue is continuously discharged, reurethanized with alcohol and recycled through the diurethane synthesis stage. A disadvantage of this procedure is firstly that the pressure distillation reactor has to be designed with sufficient size to cope with the combined streams from the bisurea synthesis and the reurethanization. However, the necessary capital costs grow proportionally to the reactor size. Secondly, the continuous recycling of the reurethanized material into the diurethane reactor complicates the setting of a defined stoichiometry which is the optimum for the diurethane preparation, because the composition of the reurethanized material varies as a function of the operating conditions. In this way, yield potential is removed from the overall process. In particular, this was observed under the conditions of the prior art in the preparation of cycloaliphatic di- or polyisocyanates. By definition, cycloaliphatic means that the isocyanate group is bonded directly to a cycloaliphatic hydrocarbon radical (e.g. cyclohexane).

In summary, it can be stated that the prior art discloses the preparation of di- and polyisocyanates by reacting appropriate starting compounds to give urethanes (one-stage or multistage) and subsequent work-up of the resulting reaction mixture which comprises the urethanes to give a urethane fraction,. subsequent cleavage of the urethanes to give the corresponding di- or polyisocyanates and isolation in pure form of this process product.

OBJECT OF THE INVENTION

It is an object of the present invention to provide an improved process for preparing cycloaliphatic diisocyanates which avoids the abovementioned disadvantages.

DETAILED DISCUSSION OF THE INVENTION

This object is achieved by a multistage and continuous process in which the formation of the diurethanes is performed in two stages, the diurethane freed of low, medium and high boilers is thermally cleaved to release the desired diisocyanates, a portion of the cleavage residue of the cleavage apparatus is continuously discharged and reurethanized with alcohol, and the reurethanized stream is recycled not into the diurethane preparation, but rather directly into the low boiler removal.

The invention provides a multistage process for continuously preparing cycloaliphatic diisocyanates, by reacting cycloaliphatic diamines with carbonic acid derivatives and alcohols to give cycloaliphatic bisureas and subsequently thermally cleaving the bisureas to give cycloaliphatic diisocyanates, which comprises performing the formation of the diurethanes in two stages, thermally cleaving the diurethane freed of low, medium and high boilers to release the desired diisocyanate, continuously discharging a portion of the cleavage residue from the cleavage apparatus and reurethanizing it with alcohol and recycling the reurethanization product directly into the low-boiler removal.

The invention also provides a multistage process for continuously preparing cycloaliphatic diisocyanates of the formula (I)

OCN—R—NCO  (I)

where R is a bivalent cycloaliphatic hydrocarbon radical having from 4 to 18, preferably from 5 to 15, carbon atoms, with the proviso that the two isocyanate groups are bonded directly to a hydrocarbon cycle and at least 3 carbon atoms are disposed between them, by reacting cycloaliphatic diamines with carbonic acid derivatives and alcohols to give diurethanes and thermally cleaving them, wherein a) cycloaliphatic diamines of the formula (II)

H$_2$N—R—NH$_2$  (II)

where R is a bivalent cycloaliphatic hydrocarbon radical having from 4 to 18, preferably from 5 to 15, carbon atoms, where the two nitrogen atoms are bonded directly to at least one hydrocarbon cycle and at least 3 carbon atoms are disposed between them, are reacted with urea and in the presence of alcohols of the formula (III)

R$^1$—OH  (III)

where R$^1$ is a radical as remains after removal of the hydroxyl group from a primary or secondary (cyclo) aliphatic alcohol having from 3 to 8 carbon atoms, in the absence or presence of catalysts, to give cycloalkylenebisureas of the formula (IV);

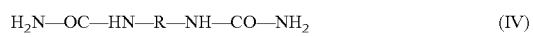

H$_2$N—OC—HN—R—NH—CO—NH$_2$  (IV)

where R is a bivalent cycloaliphatic hydrocarbon radical having from 4 to 18, preferably from 5 to 15, carbon atoms, with the proviso that the two nitrogen atoms adjacent to R are bonded directly to a hydrocarbon cycle and at least 3 carbon atoms are disposed between them, and the ammonia formed is simultaneously removed continuously;

b) the resulting crude cycloalkylenebisurea is converted in a second reactor using the alcohol of the formula (III) as a solvent while continuously driving out the ammonia released to cycloalkylenediurethane of the formula (V)

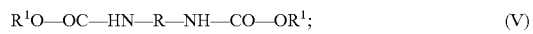

R$^1$O—OC—HN—R—NH—CO—OR$^1$;  (V)

c) the alcohol, the dialkyl carbonates and/or alkyl carbamates are removed from the resulting reaction mixture, and the alcohol is recycled into the reaction stage a);

d) the material stream from stage c) is separated by distillation into a material-of-value stream and a by-product stream which is discharged, e) the reaction mixture comprising the diurethanes purified by steps b) and d) is continuously and thermally cleaved in the presence of a catalyst and without solvent, at temperatures of from 180 to 280° C., preferably from 200 to 260° C., and under a pressure of from 0.1 to 200 mbar, preferably from 0.2 to 100 mbar, in such a way that a portion of the reaction mixture of from 10 to 60% by weight based on the feed, preferably from 15 to 45% by weight based on the feed, is constantly discharged;

f) the cleavage products are separated by rectification into crude diisocyanate and alcohol;

g) the crude cycloaliphatic diisocyanate, purified by distillation, and the pure product fraction are isolated;

h) the bottoms discharge from e) is reacted with the alcohol from f) in the presence or absence of catalysts within from 1 to 150 min, preferably from 3 to 60 min, at temperatures of from 20 to 200° C., preferably from 50 to 170° C., and a pressure of from 0.5 to 20 bar, preferably from 1 to 15 bar, at a molar ratio of NCO groups to OH groups of up to 1:100, preferably 1:20 and more preferably 1:10;

i) the reurethanization reaction h) may be carried out under the conditions already described, also in the presence of specific catalysts selected from halides of Fe(III) and/or Cu(I);

j) a portion of the bottoms fraction of the purification by distillation g) is continuously discharged and conducted into the cleavage reaction e) and/or into the urethanization stage h);

k) optionally, the top fraction obtained in the purification by distillation of the crude cycloaliphatic diisocyanate is likewise recycled into the urethanization stage h);

l) the reurethanized stream from h) is recycled into stage c).

In the process according to the invention, cycloaliphatic diisocyanates can be prepared continuously, without any problem and in very good yield. The dispensation with the recycling of the reurethanized stream having a variable composition into the diurethane preparation results in two advantages for the multistage process according to the invention. Firstly, the diurethane reactor is burdened with a lower volume flow rate compared to the prior art, so that a smaller design of the reactor allows cost saving potential to be raised. Secondly, it is ensured that the diurethane synthesis can be carried out at any time under defined stoichiometric ratios which have been optimized in the context of the yield.

a) To prepare the cycloalkylenebisureas of the formula (IV) in reaction stage a), the cycloaliphatic diamines of the formula (II) are reacted with urea in the presence of an alcohol of the formula (III), in some cases also mixtures of such alcohols, in a reactor at from 100 to 145° C. and a pressure of from 0.7 to 1.8 bar, in the course of which the ammonia formed is continuously driven out. The reaction is effected preferably in a distillation reactor, by introducing the reactant in a molar diamine:urea:alcohol ratio of 1:2.0 to 2.4:3 to 10 continuously to the uppermost tray and driving out the ammonia released by alcohol vapors which are introduced in the bottom of the distillation reactor.

The residence time required is from 4 to 10 hours, preferably from 5 to 9 hours. The amount of alcohol introduced in the bottom to drive out the ammonia is from 0.05 to 3 kg/kg, preferably from 0.1 to 1 kg/kg, of bisurea, and the amount of alcohol introduced in this way is removed at the top together with ammonia formed, freed of residual ammonia by partial condensation in an alcohol recovery column, and recycled into the bottom.

b) The crude cycloalkylenebisurea dissolved in alcohol which is obtained at the bottom of the distillation reactor is conducted continuously into a second reactor in which the conversion to the diurethane proceeds at elevated temperature and elevated pressure, in the course of which ammonia is again released and has to be removed from the reaction mixture for reasons of chemical equilibrium. The further conversion of the crude cycloalkyleneurea from a) is effected preferably in a pressure distillation reactor and at a molar ratio of bisurea to alcohol of from 1:5 to 12. The material stream from a) is preferably conducted continuously to the uppermost tray of the pressure distillation reactor. The conversion takes place in the absence or presence of catalysts, at reaction temperatures of 140 to 270° C., preferably 160 to 250° C., and under a pressure which is between 5 to 20 bar, preferably 7 to 15 bar, within from 2 to 20 hours, preferably 8 to 15 hours. The continuous driving out of the ammonia released is promoted by alcohol vapors which are introduced in the bottom of the pressure distillation reactor and are appropriately generated in an evaporator mounted at the bottom of the column.

To increase the reaction rate, the diurethanes may be prepared in the presence of catalysts. Suitable catalysts are inorganic or organic compounds which contain one or more, preferably a cation of, metals or Groups 1-15, in accordance with the IUPAC-recommended Periodic Table of the Elements; for example halides such as chlorides and bromides, sulfates, phosphates, nitrates, borates, alkoxides, phenoxides, sulfonates, oxides, oxide hydrates, hydroxides, carboxylates, chelates, carbonates and thio- or dithiocarbamates. Examples include the cations of the following metals: lithium, sodium, potassium, magnesium, calcium, aluminum, gallium, tin, lead, bismuth, antimony, copper, silver, gold, zinc, mercury, cerium, titanium, vanadium, chromium, molybdenum, manganese, iron, cobalt and nickel. Examples of typical catalysts include the following compounds: lithium ethoxide, lithium butoxide, sodium methoxide, potassium tert-butoxide, magnesium ethoxide, calcium methoxide, tin(II) chloride, tin(IV) chloride, lead acetate, aluminum trichloride, bismuth trichloride, copper(II) acetate, copper(II) chloride, zinc chloride, zinc octoate, titanium tetrabutoxide, vanadium trichloride, vanadium acetylacetonate, manganese(II) acetate, iron(II) acetate, iron (III) acetate, iron oxalate, cobalt chloride, cobalt naphthenate, nickel chloride, nickel naphthenate and mixtures thereof. The catalysts may optionally also be used in the form of their hydrates or ammoniates.

Starting compounds for the process according to the invention are diamines of the formula (II) which has already been mentioned above, alcohols of the formula (III) which has already been mentioned above, and also urea. Suitable diamines of the formula (II) are, for example, 1,4-diaminocyclohexane, 4,4'-dicyclohexylmethanediamine, 2,4-dicyclohexylmethanediamine, 2,2'-dicyclohexylmethanediamine and isomeric cycloaliphatic diamines, and also perhydrogenated diphenylmethanediamine. As a result of the preparation, diphenylmethanediamine (MDA) occurs as an isomer mixture of 4,4'-, 2,4- and 2,2'-MDA (see, for example, DE 10127273). Perhydrogenated diphenylmethanediamine is obtained by fully hydrogenating MDA and is accordingly a mixture of isomeric dicyclohexylmethanediamines ($H_{12}$MDA), i.e. 4,4'-, 2,4- and 2,2'-$H_{12}$MDA. The diamines of the formula (II) used are preferably 4,4'-dicyclohexylmethanediamine, 2,4-dicyclohexylmethanediamine and 2,2'-dicyclohexylmethanediamine, and also any mixtures of at least two of these isomers. It will be appreciated that diamines may also be used which deviate from the formula (II). Examples include 1,3- and 1,4-diaminomethylcyclohexane, 1,6-hexanediamine, 2,2,4- or 2,4,4-trimethyl-1,6-hexanamine and 3-aminomethyl-3,5,5-trimethylcyclohexylamine. However, preference is not given to using amines which deviate from the formula (II).

Suitable alcohols of the formula (III) are any aliphatic or cycloaliphatic alcohols which have a boiling point below 190° C. under atmospheric pressure. Examples include C1-C6-alkanols, for example methanol, ethanol, 1-propanol, 1-butanol, 2-butanol, 1-hexanol or cyclohexanol. The alcohol used is preferably 1-butanol.

In the course of the conversion of the reaction mixture, ammonia is released, whose removal from the reaction equilibrium has been found to be advantageous. When ammonia is discharged from the reactor, care has to be taken that the wall temperatures of the reactor and of the discharge tube are above 60° C., so that deposition of ammonium carbamate, which is formed in minimal amounts from ammonia and carbon dioxide by decomposition of urea, can be prevented. It has been found to be useful, for example, to carry out the reaction in a pressure distillation reactor, in which case the reaction mixture is conducted in countercurrent to alcohol vapors introduced in the bottom and in this way such intensive mixing of the liquid proceeds on the trays that they each virtually correspond to a battery stage. The vaporous mixture of alcohol and ammonia which is withdrawn at the top may, preferably under the pressure of the pressure distillation reactor and without condensing it beforehand, be conducted into a distillation column, in order, from the ammonia, to obtain free alcohol which is recycled into the bottom of the pressure distillation reactor and of the column. In order to prevent fouling of the reflux condenser with ammonium carbamate, an appropriate proportion of alcohol is permitted therein to set the temperature at the top to at least 60° C.
c) The excess alcohol, the dialkyl carbonates, if they have been formed, or mixtures of at least two of these components are removed in one, or advantageously two, stages. At the first stage, the reaction mixture is decompressed from the pressure level of reaction stage b) to a pressure of from 1 to 500 mbar, preferably from 2 to 150 mbar, and in this way separated into gaseous vapors which contain the predominant amount of alcohol and also any dialkyl carbonates and/or alkyl carbamates, and into a liquid effluent. In the second stage, the liquid effluent is freed of any remaining residual butanol and also medium boilers such as dialkyl carbonates and/or alkyl carbamates by thin-film evaporation at from 180 to 250° C., preferably from 200 to 230° C., and a pressure of from 0.1 to 20 mbar, preferably from 1 to 10 mbar, so that the residue consists substantially of the monomeric diurethane, and in some cases high-boiling oligomers. The vapors may, after further distillative purification, be recycled into reaction stage a).
d) The liquid stream which contains the monomeric diurethanes and any high-boiling oligomers and is obtained after the removal of the vapors from step c) is separated, preferably with the aid of a thin-film or short-path evaporator, at a temperature of from 180 to 260° C., preferably from 200 to 240° C., and under a pressure of from 0.01 to 10 mbar, preferably from 0.02 to 5 mbar, by distillation into a material-of-value stream which contains the monomeric diurethanes and the lower-boiling by-products and a nondistillable by-product stream which is discharged from the preparative process and is typically discarded as a residue whose material cannot be utilized.

Optionally, the stream from stage c) which contains any high-boiling oligomers, before its above-described distillative purification, may also be divided into two substreams of which one is fed directly to the deblocking reaction (see e)) and the other initially passes through the high boiler removal already described.
e) The material-of-value stream which contains the monomeric diurethanes and the lower-boiling by-products is partly and continuously thermally cleaved in a suitable apparatus, without solvents in the liquid phase in the presence of catalysts at temperatures of from 180 to 280° C., preferably from 200 to 260° C., and under a pressure of from 0.1 to 200 mbar, preferably from 0.2 to 100 mbar. The conversion of diurethane to diisocyanate in the apparatus for thermal cleavage may, depending on the diurethane used, be selected substantially freely and is typically within the range of from 10 to 95% by weight, preferably from 35 to 85% by weight of the diurethane feed. The uncleaved proportion of the reaction mixture which contains unconverted diurethanes, high-boiling by-products and other reutilizable and nonutilizable by-products is continuously discharged. The amount of the discharge is governed, inter alia, by the desired conversion and the desired capacity of the cleavage reaction and can be easily determined experimentally. It is typically from 10 to 60% by weight, preferably from 15 to 45% by weight, based on the feed.

Useful catalysts for chemically cleaving the diurethanes are, for example, the aforementioned inorganic and organic compounds which catalyze urethane formation. Preference is given to using chlorides of zinc or tin, and also zinc oxides, manganese oxides, iron oxides or cobalt oxides, in which case the catalyst is metered into the stream from the purification step d), before it is fed into the cleavage, as a from 0.01 to 25% by weight, preferably from 0.05 to 10% by weight, solution or suspension, into the alcohol which is also used for urethane preparation, in an amount of from 5 to 400 ppm, preferably from 10 to 100 ppm.

Suitable cleavage apparatus is, for example, cylindrical cleavage reactors, for example tubular furnaces or preferably evaporators such as falling-film, thin-film or bulk evaporators, selected from Robert evaporators, Herbert evaporators, Caddle-type evaporators, Oskar evaporators and heating cartridge evaporators.

In principle, the main concern is to keep the average residence time of isocyanate groups, which are inevitably released when the alcohol is deblocked, in the cleavage zone very low and thus to limit undesired side reactions to a minimum.

Preference is given to carrying out the cleavage in a combined cleavage and rectification column, which is equipped for the energy supply in the bottom with a falling-film evaporator, in the lower third with a unit for additional energy input or for energy recovery, in the upper third with a unit to remove preferably crude diisocyanate and at the top with a condenser for the reflux and the removal of pure alcohol.
f) The cleavage products which are formed in the thermal cleavage and are composed in particular of alcohol, diisocyanate and partially cleaved diurethanes are separated by rectification at from 95 to 260° C., preferably from 110 to 245° C., and a pressure of from 0.5 to 250 mbar, preferably from 1 to 100 mbar, into alcohol and into a crude diisocyanate mixture, consisting of cycloaliphatic diisocyanate, partially cleaved cycloaliphatic diisocyanate and in some cases small amounts of cycloaliphatic diurethane. This separation may be carried out, for example, in the cleavage column of the abovementioned combined cleavage and rectification column.
g) The crude mixture which is preferably obtained by rectification, consisting of cycloaliphatic diisocyanate, partially cleaved cycloaliphatic diurethane and in some cases small fractions of cycloaliphatic diurethane, is purified by distillation at a temperature of from 95 to 260° C., preferably from 110 to 245° C., and under a pressure of from 0.5 to 150 mbar, preferably from 1 to 75 mbar, and the resulting fractions are recycled or isolated as a pure product.
h) The bottoms discharge from the deblocking stage e) is combined with the alcohol from the rectification stage f), in a molar ratio of NCO groups to OH groups of up to 1:100, preferably 1:20 and more preferably 1:10, and the reaction mixture is converted, in the presence or absence of catalysts, within from 1 to 150 min, preferably from 3 to 60 min, at temperatures of from 20 to 200° C., preferably from 50 to 170° C., and a pressure of from 0.5 to 20 bar, preferably from 1 to 15 bar. The reaction may be carried out in a continuous tank battery or in a tubular reactor. Useful catalysts are in principle all catalysts which support the NCO/OH reaction. Examples include tin octoate, dibutyltin laurate, tin dichloride, zinc dichloride and triethylamine.
i) The reurethanization reaction h) may be carried out under the conditions already described, also in the presence of specific catalysts selected from halides of Fe(II) and/or Cu(I).
j) A portion of the bottoms fraction of the purifying distillation g) is continuously discharged and optionally recycled into the deblocking stage e) or into the urethanization stage h). Preference is given to recycling into the urethanization stage. The amount of the discharge is from 0.1 to 50% by weight, preferably from 0.2 to 25% by weight, of the feed of crude diisocyanate into the purifying distillation stage.

k) The top fraction of the purifying distillation stage g) may be discarded or preferably recycled into the urethanization stage h). The amount of top fraction removed per unit time is from 0.1 to 3% by weight, preferably from 0.3 to 1% by weight, of the feed of crude diisocyanate into the purifying distillation.

l) The stream from the urethanization stage g) is recycled into the low and medium boiler removal c).

The multistage process according to the invention for continuously preparing cycloaliphatic diisocyanates with recycling and discharge of the by-products allows, for distillable cycloaliphatic diisocyanates, a reaction which proceeds without disruption and with high selectivity to be ensured. The process according to the invention is suitable in particular for preparing cycloaliphatic diisocyanates having from 4 to 18, preferably from 5 to 15, carbon atoms, such as 1,4-diisocyanatocyclohexane, 4,4'-dicyclohexylmethane diisocyanate (4,4'-$H_{12}$MD), 2,2'-dicyclohexylmethane diisocyanate (2,2'-$H_{12}$MDI), 2,4'-dicyclohexylmethane diisocyanate (2,4'-$H_{12}$MDI) or else mixtures of the aforementioned isomeric dicyclohexylmethane diisocyanates ($H_{12}$MDI), as are obtained, for example, by the nature of the conversion of perhydrogenated MDA to $H_{12}$MDI. Very particular preference is given to preparing 4,4'-dicyclohexylmethane diisocyanate and any mixtures of 4,4'-$H_{12}$MDI, 2,4-$H_{12}$MDI and 2,2'-$H_{12}$MDI.

The cycloaliphatic diisocyanates prepared are excellently suited to preparing polymers containing urethane, isocyanurate, amide and/or urea groups by the polyisocyanate polyaddition process. They additionally find use for preparing polyisocyanate mixtures modified with urethane, biuret and/or isocyanurate groups. Such polyisocyanate mixtures of cycloaliphatic diisocyanates are used in particular for preparing high-value, light-resistant polyurethane coatings.

For example, polymers containing urethane may be prepared by reacting the prepared cycloaliphatic disocyanates with at least one polyol. At least one polyol may be selected from known polyols usually used in the production of polyurethanes.

Known polyols are those compounds that include dihydric alcohols having 2 to 20 carbon atoms (aliphatic diols, for instance, alkylene glycols such as ethylene glycol, diethylene glycol, propylene glycol, 1,3- or 1,4-butanediol, 1,6-hexanediol, and neopentylglycol; and alicyclic diols, for instance, cycloalkylene glycols such as cyclohexanediol and cyclohexanedimethanol); trihydric alcohols having 3 to 20 carbon atoms (aliphatic triols, for instance, alkane triols such as glycerol, trimethylolpropane, trimethylolethane, and hexanetriol, and triethanolamine); polyhydric alcohols having 4 to 8 hydroxyl groups and 5 to 20 carbon atoms (aliphatic polyols, for instance, alkane polyols and intramolecular or intermolecular dehydration products of the same such as pentaerythritol, sorbitol, mannitol, sorbitan, diglycerol, and dipentaerythritol; and saccharides and derivatives of the same such as sucrose, glucose, mannose, fructose, and methylglucoside).

Other mentionable polyols include monocyclic polyhydric phenols such as pyrogallol, hydroquinone and phloroglucinol; bisphenols such as bisphenol A, bisphenol F and bisphenol sulfone; and condensation products of phenols and formaldehyde (novolak).

Additionally, the above-mentioned polyols may include oligomers or polymers of alkylene oxides having 2 to 8 carbon atoms. The alkylene oxides include ethylene oxide, propylene oxide, 1,2-, 1,4-, 1-3, or 2,3-butylene oxide, styrene oxide, and the like.

Moreover, the above-mentioned polyols may include co-oligomers or co-polymers of alkylene oxides having 2 to 8 carbon atoms; wherein the alkylene oxides include combinations of two or more of ethylene oxide, propylene oxide, 1,2-, 1,4-, 1-3, or 2,3-butylene oxide, styrene oxide in block addition and/or random addition. Preferably, propylene oxide or a combination of propylene oxide and ethylene oxide (containing not more than 25 mass % of ethylene) is used.

Other examples of polyols include, but are not limited to, for example, aminic polyols such as JEFFAMINE™ as described in U.S. Pat. No. 5,418,260.

Having generally described this invention, a further understanding can be obtained by reference to certain specific examples which are provided herein for purposes of illustration only, and are not intended to be limiting unless otherwise specified.

EXAMPLES

Example 1

Preparation According to the Invention of Dicyclohexylmethane Diisocyanate ($H_{12}$MDI) from Perhydrogenated Diphenylmethanediamine and Urea in the Presence of n-butanol Every hour, the uppermost tray of a distillation reactor was charged with 263.0 g of $H_{12}$MDA, 154.5 g of urea and 555.9 g of n-butanol, and the reaction mixture was boiled at 135° C. and an average residence time of 8 hours while continuously removing the ammonia released at atmospheric pressure. The solution of bisurea in butanol which was obtained in the bottom of the distillation reactor was preheated to 190° C. using a heat exchanger, conducted to the uppermost tray of a pressure distillation reactor and further converted at from 11 to 14 bar, 220° C. and with an average residence time of 10.5 h. In the bottom of the pressure distillation reactor, 506.8 g per hour of n-butanol were fed in and the amount of alcohol removed at the top together with ammonia released was selected in such a way that it corresponded to the alcohol input in the bottom. The reactor effluent, together with the stream from the reurethanization, was subsequently freed of excess alcohol, low boilers and medium boilers in the flash vessel at 55 mbar with subsequent thin-film evaporation at 220° C. and 2 mbar, and fed to high boiler removal by short-path evaporation at 0.08 mbar. The remaining 628.7 g/h of bis(4-butoxycarbonylaminocyclohexyl)methane ($H_{12}$MDU) were conducted as a melt (140° C.) into the circulation of the falling-film evaporator of the cleavage and rectification column, and the deblocking reaction was carried out at a temperature of 237° C. and a bottom pressure of 10 mbar in the presence of a steady-state concentration of tin dichloride of 18 ppm. The cleavage gases, $H_{12}$MDI and butanol, were condensed out in two condensers connected in series at 85° C. and −25° C. The resulting about 97% crude $H_{12}$MDI was fed to a purifying distillation where 281.16 g/h of $H_{12}$MDI having a purity of >99.5% were obtained, which corresponds to a yield of 86% based on the amine. 183.2 g/h of butanol were obtained as the top product of the cleavage and rectification column. To maintain constant mass within the cleavage and rectification column and avoid fouling and blockages of the cleavage apparatus, 156.1 g/h were continuously discharged from the circuit and combined together with 22.2 g/h of material separated from the bottoms of the $H_{12}MDI$ purifying distillation, and also the top product from the cleavage and rectification column, and reurethanized. The reurethanized material was fed to the flash vessel together with the reactor effluent of the diurethane preparation.

Example 2

Preparation According to the Invention of Dicyclohexylmethane Diisocyanate ($H_{12}MDI$) from Perhydrogenated Diphenylmethanediamine and Urea in the Presence of n-butanol—Reurethanization in the Presence of CuCl and Recycling of the Reurethanized Material into the Low and Medium Boiler Removal Every hour, the uppermost tray of a distillation reactor was charged with 263.1 g of $H_{12}MDA$, 154.5 g of urea and 555.1 g of n-butanol, and the reaction mixture was boiled while continuously removing the ammonia released at atmospheric pressure, 135° C. and an average residence time of 8 hours. The solution of bisurea in butanol which was obtained in the bottom of the distillation reactor was preheated to 190° C. using a heat exchanger, conducted to the uppermost tray of a pressure distillation reactor and further converted at from 11 to 14 bar, 220° C. and with an average residence time of 10.5 h. In the bottom of the pressure distillation reactor, 510.3 g per hour of n-butanol were fed in and the amount of alcohol removed at the top together with ammonia released was selected in such a way that it corresponded to the alcohol input in the bottom. The reactor effluent, together with the stream from the reurethanization, was freed at 220° C. and 2 mbar of excess alcohol, low and medium boilers in the flash vessel at 55 mbar with subsequent thin-film evaporation and the high boiler removal was carried out by short-path evaporation at 220° C. and 2 mbar. The remaining 631.5 g/h of bis(4-butoxycarbonylaminocyclohexyl)methane ($H_{12}MDU$) were conducted as a melt (140° C.) into the circulation of the falling-film evaporator of the cleavage and rectification column, where the deblocking reaction was carried out at a temperature of 235° C. and a bottom pressure of 10 mbar in the presence of a steady-state concentration of tin dichloride of 15 ppm. The cleavage gases, $H_{12}MDI$ and butanol, were condensed out in two condensers connected in series at 85 and −25° C. The resulting about 97% crude $H_{12}MDI$ was fed to a purifying distillation to obtain 284.28 g/h of $H_{12}MDI$ having a purity of >99.5%, which corresponds to a yield of 87% based on the amine. 186.3 g/h of butanol were obtained as the top product of the cleavage and rectification column. To maintain constant mass within the cleavage and rectification column and prevent fouling and blockages of the cleavage apparatus, 154.8 g/h were continuously discharged from the circuit and combined together with 21.9 g/h of material separated from the bottoms of the $H_{12}MDI$ purifying distillation, and also the top product from the cleavage and rectification column, and reurethanized in the presence of 100 ppm of CuCl. The reurethanized material was fed to the diurethane preparation in the flash vessel.

This application is based on DE Application No. 10338509.6, filed with the German patent office on Aug. 22, 2003, the entire contents of which is hereby incorporated herein by reference.

Obviously, numerous modifications and variations on the present invention are possible in light of the above teachings. It is therefore to be understood that within the scope of the appended claims, the invention may be practiced otherwise than as specifically:

What is claimed as new and is intended to be secured by Letters Patent is:

1. A multistage process for continuously preparing cycloaliphatic diisocyanates, which comprises:
    reacting cycloaliphatic diamines with carbonic acid derivatives and alcohols to give cycloaliphatic diurethane and subsequently
    thermally cleaving the cycloaliphatic diurethane to give cycloaliphatic diisocyanates,
    wherein said process comprises producing diurethanes in two stages, thermally cleaving the cycloaliphatic diurethane freed of low, medium and high boilers to release the desired cycloaliphatic diisocyanate, and continuously discharging a portion of a cleavage residue from a cleavage apparatus and reurethanizing the cleavage residue with alcohol and recycling the reurethanization product directly into a low-boiler separation.

2. The multistage process of claim 1, wherein the cycloaliphatic diamine is selected from the group consisting of 4,4'-dicyclohexylmethanediamine, 2,4-dicyclohexylmethanediamine 2,2'-dicyclohexylmethanediamine, and mixtures thereof.

3. The multistage process of claim 1, wherein the cycloaliphatic diamine is selected from the group consisting of 4,4'-dicyclohexylmethanediamine, isomeric cycloaliphatic diamines, and mixtures thereof.

4. The multistage process of claim 1, wherein the cycloaliphatic diamine is 1,4-diaminocyclohexane.

5. A multistage process for continuously preparing cycloaliphatic diisocyanates of the formula (I)

$$OCN\text{—}R\text{—}NCO \qquad (I)$$

where R is a bivalent cycloaliphatic hydrocarbon radical having from 4 to 18 carbon atoms, with the proviso that the two isocyanate groups are bonded directly to a hydrocarbon cycle and at least 3 carbon atoms are disposed between them, which comprises:

a) reacting a cycloaliphatic diamine represented by formula (II)

$$H_2N\text{—}R\text{—}NH_2 \qquad (II)$$

wherein R is a bivalent cycloaliphatic hydrocarbon radical having from 4 to 18 carbon atoms, where the two nitrogen atoms are bonded directly to at least one hydrocarbon cycle and at least 3 carbon atoms are disposed between them;
with urea in the presence of at least one alcohol represented by formula (III), $$R^1\text{—}OH \qquad (III)$$

wherein $R^1$ is a radical, which remains after removal of the hydroxyl group, from a primary or secondary (cyclo)aliphatic alcohol having from 3 to 8 carbon atoms;
in the absence or presence of catalysts to yield cycloalkylenebisureas represented by formula (IV);

$$H_2N\text{—}OC\text{—}HN\text{—}R\text{—}NH\text{—}CO\text{—}NH_2 \qquad (IV)$$

wherein R is a bivalent cycloaliphatic hydrocarbon radical having from 4 to 18 carbon atoms, with the proviso that the two nitrogen atoms adjacent to R are bonded directly to a hydrocarbon cycle and at least 3 carbon atoms are disposed between them, and the ammonia formed is simultaneously removed continuously;

b) converting the resulting crude cycloalkylenebisurea represented by formula (IV) in a second reactor in the presence of a solvent comprising at least one alcohol represented by formula (III), while continuously driving out the ammonia produced during the converting to cycloalkylenediurethane of the formula (V)

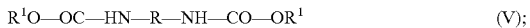
R¹O—OC—HN—R—NH—CO—OR¹ (V);

c) removing at least one alcohol, dialkyl carbonate, and alkyl carbamate from the resulting reaction mixture, and recycling the alcohol into the reaction stage a);

d) distilling a material stream obtained during stage c) into a material-of-value stream comprising cycloalkylenediurethane and a by-product stream which is discharged;

e) continuously and thermally cleaving a reaction material comprising purified cyclalkylenediurethane obtained by stages c) and d), in a manner such that a portion of the reaction mixture of from 10 to 60% by weight based on the feed, is constantly discharged; wherein the continuously and thermally cleaving occurs at temperatures of from 180 to 280° C., and under a pressure of from 0.1 to 200 mbar;

f) separating the cleavage products by rectification into a crude diisocyanate and alcohol;

g) purifying the crude cycloaliphatic diisocyanate by distillation, and isolating the pure product fraction;

h) reacting the bottoms discharge from stage e) with the alcohol from stage f) in the presence or absence of catalysts within from 1 to 150 min, at temperatures of from 20 to 200° C., and a pressure of from 0.5 to 20 bar, at a molar ratio of NCO groups to OH groups of up to 1:100;

i) wherein the reurethanization reaction, stage h), optionally occurs in the presence of a catalyst selected from the group consisting of a halide of Fe(III), Cu(I), and mixtures thereof;

j) continuously discharging and conducting a portion of the bottoms fraction obtained from distillation of stage g) into the cleavage reaction e), into the reurethanization stage h), or both the cleavage reaction e) and the reurethanization stage h);

k) optionally recycling the top fraction obtained in the purification by distillation of the crude cycloaliphatic diisocyanate, stage g), into the urethanization stage h); and l) recycling the reurethanized stream from stage h) into stage c).

6. The process of claim 5, wherein stage a) occurs in a reactor at from 100 to 145° C. and a pressure of from 0.7 to 1.8 bar.

7. The process of claim 5, wherein stage a) occurs in a distillation reactor.

8. The process of claim 5, wherein stage a) occurs having a molar ratio of diamine:urea:alcohol of from 1:2.0 to 2.4:3 to 10.

9. The process of claim 5, wherein stage a) further comprises
continuously supplying at least one reactant to the uppermost tray and
removing ammonia produced during the reacting by introducing alcohol vapors into the bottom of the distillation reactor.

10. The process of claim 5, wherein the residence time of the reactants in stage a) is from 4 to 10 hours.

11. The process of claim 5, wherein stage b) occurs in a pressure distillation reactor.

12. The process of claim 5, wherein stage b) occurs having a molar ratio of bisurea to alcohol of from 1:5 to 12.

13. The process of claim 5, which further comprises conducting a stream from stage a) to an uppermost tray of the second reactor of stage b).

14. The process of claim 5, which further comprises continuously conducting a stream from stage a) to an uppermost tray of the second reactor of stage b).

15. The process of claim 5, wherein the converting that occurs in stage b) occurs at about a reaction temperature of from 40 to 270° C., and under a pressure of from 5 to 20 bar.

16. The process of claim 5, wherein the reacting in stage a) and/or the converting in stage b) occurs in the presence of at least one catalyst.

17. The process of claim 5, wherein stage c) comprises two stages.

18. The process of claim 17, wherein, at the first stage comprises decompressing the reaction mixture from a pressure level of reaction stage b) to a pressure of from 1 to 500 mbar.

19. The process of claims 17, which further comprises feeding vapors obtained from stage c), after further distillative purification, into reaction stage a).

20. The process of claim 5, wherein the separating in stage d) occurs at a temperature of from 180 to 260° C., and under a pressure of from 0.01 to 10 mbar.

21. The process of claim 5, wherein stage d) occurs with the aid of a thin-film or short-path evaporator.

22. The process of claim 5, wherein stage d) further comprises discarding the by-product stream.

23. The process of claim 5, wherein stage c) further comprises
dividing a stream, prior to distilling and purifying, into two substreams; and
conducting one substream directly into stage e).

24. The process of claim 5, wherein stage e) occurs in a combined cleavage and rectification column.

25. The process of claim 5, wherein, in stage e), occurs in the presence of at least one catalyst, and thermal cleavage occurs continuously at temperatures of from 180 to 280° C., and under a pressure of from 0.1 to 200 mbar.

26. The process of claim 5, wherein, in stage e), cleavage occurs without added solvent in the liquid phase.

27. The process of claim 5, wherein stage e) occurs in the presence of at least one catalyst.

28. The process of claim 5, wherein, in stage e), the thermally induced diurethane cleavage occurs in at least one tubular furnace or at least one evaporator.

29. The process of claim 28, wherein cleavage occurs in at least one evaporator which is selected from the group consisting of falling-film, thin-film, bulk evaporators, and combinations thereof.

30. The process of claim 5, wherein, in stage e), the conversion of diurethane to diisocyanate occurs depending on the diurethane used.

31. The process of claim 5, wherein, in stage e), the conversion of diurethane to diisocyanate occurs within the range of from 10 to 95% by weight of the diurethane feed.

32. The process of claim 5, wherein stage e) further comprises
continuously discharging a portion of the reaction mixture which comprises unconverted diurethanes, high-boiling by-products and other reutilizable and nonutilizable by-products, and mixtures thereof.

33. The process of claim 32, wherein the amount of the discharge is from 10 to 60% by weight based on the feed.

34. The process of claim 5, wherein stage h) occurs in a continuous tank battery or in a tubular reactor.

35. The process of claim 5, wherein the reaction in stage h) occurs in the presence of at least one catalyst selected from the group consisting of a tin carboxylate, a zinc carboxylate, a tin halide, a zinc halide, a complex comprising tin and a tertiary amine, a complex comprising zinc and a tertiary amine, and combinations thereof.

36. The process of claim 5, wherein, in stage j), the amount of the discharge is from 0.1 to 50% by weight of the feed of crude diisocyanate into the purifying distillation.

37. The process of claim 5, which further comprises
recycling the top fraction obtained in the purification by distillation of the crude cycloaliphatic diisocyanate, stage g), into the urethanization stage h).

38. The process of claim 5, wherein the prepared cycloaliphatic diisocyanate is selected from the group consisting of 1,4-diisocyanatocyclohexane, 4,4'-dicyclohexylmethane diisocyanate, 2,2'-dicyclohexylmethane diisocyanate, 2,4'-dicyclohexylmethane diisocyanate, and mixtures of at least two isomeric dicyclohexylmethane diisocyanates, and mixture thereof.

39. The process of claim 5, wherein the cycloaliphatic diamine is selected from the group consisting of 1,3-diaminomethylcyclohexane; 1,4-diaminomethylcyclohexane; 2,4,4-trimethylhexanediamine-1,6; 2,4,4-trimethylhexanediamine-1,6; 2-aminomethyl-3,5,5-trimethylcyclohexylamine, and mixtures thereof.

40. A process for producing polyurethane, which comprises:
reacting the cycloaliphatic diisocyanate as claimed in claim 1 with a polyol.

41. A process for producing polyurethane, which comprises:
reacting the cycloaliphatic diisocyanate as claimed in claim 1 with a diol.

42. A process for producing polyurethane, which comprises:
reacting the cycloaliphatic diisocyanate as claimed in claim 5 with a polyol.

43. A process for producing polyurethane, which comprises:
reacting the cycloaliphatic diisocyanate as claimed in claim 5 with a diol.

* * * * *